(12) United States Patent
Weckwerth et al.

(10) Patent No.: US 8,518,027 B2
(45) Date of Patent: Aug. 27, 2013

(54) PHOTOTHERAPY DEVICE THERMAL CONTROL APPARATUS AND METHOD

(75) Inventors: Mark V. Weckwerth, Pleasanton, CA (US); Charles A. Schuetz, Oakland, CA (US); Harvey I. Liu, Fremont, CA (US); Patrick Reichert, Dublin, CA (US); Tobin C. Island, Oakland, CA (US); Robert E. Grove, Pleasanton, CA (US)

(73) Assignee: Tria Beauty, Inc., Dublin, CA (US)

( * ) Notice: Subject to any disclaimer, the term of this patent is extended or adjusted under 35 U.S.C. 154(b) by 663 days.

(21) Appl. No.: 12/607,280

(22) Filed: Oct. 28, 2009

(65) Prior Publication Data

US 2011/0098789 A1    Apr. 28, 2011

(51) Int. Cl.
*A61B 18/18* (2006.01)
*A61N 5/06* (2006.01)

(52) U.S. Cl.
USPC ............ 606/2; 606/3; 606/4; 606/5; 606/6; 606/7; 606/8; 606/9; 606/10; 607/88; 607/89; 607/90; 607/91; 607/92; 607/93; 607/94; 128/898

(58) Field of Classification Search
USPC ............ 606/2–19; 607/88–94; 128/898
See application file for complete search history.

(56) References Cited

U.S. PATENT DOCUMENTS

| | | | |
|---|---|---|---|
| 5,743,901 A * | 4/1998 | Grove et al. | 606/9 |
| 6,235,015 B1 | 5/2001 | Mead, III et al. | 606/9 |
| 2005/0171581 A1 | 8/2005 | Connors et al. | 607/88 |
| 2005/0231965 A1 | 10/2005 | Ostler et al. | 362/456 |
| 2006/0009749 A1 * | 1/2006 | Weckwerth et al. | 606/9 |
| 2008/0027518 A1 * | 1/2008 | Island et al. | 607/88 |
| 2009/0018628 A1 * | 1/2009 | Burns et al. | 607/101 |
| 2009/0043294 A1 * | 2/2009 | Island et al. | 606/9 |

FOREIGN PATENT DOCUMENTS

| | | |
|---|---|---|
| WO | 99/46005 | 3/1999 |
| WO | 01/26573 A1 | 4/2001 |
| WO | 2006/089227 A2 | 8/2006 |
| WO | 2008/097062 A1 | 8/2008 |
| WO | 2009/014312 A1 | 1/2009 |

OTHER PUBLICATIONS

International PCT Search Report, PCT/US2010/053755, 14 pages.

* cited by examiner

*Primary Examiner* — Jessica Stultz
*Assistant Examiner* — Delma R Forde
(74) *Attorney, Agent, or Firm* — King & Spalding L.L.P.

(57) ABSTRACT

A phototherapy device includes a light source; a light emanation block; and a heat exchanger for the dissipation of heat from one or more heat loads associated with the device. Heat may be transferred via the heat exchanger from the light source independently of the dissipation of heat from one or more of the other device heat loads. Substantially thermally isolated heat transfer regions may be provided, and such regions may be maintained at different operating temperatures, to control the transfer of heat in conjunction with a phototherapy method and to promote efficient and enhanced device operation and performance.

19 Claims, 9 Drawing Sheets

US 8,518,027 B2

PHOTOTHERAPY DEVICE THERMAL CONTROL APPARATUS AND METHOD

TECHNICAL FIELD

The invention relates generally to a thermal control apparatus and method, and more particularly, in accordance with one range of embodiments, to an apparatus and method for controlling the transfer of heat in a phototherapy device.

BACKGROUND

A phototherapy device is an apparatus that includes one or more sources of light energy. A phototherapy device typically generates light energy for a particular desired purpose. For example, a phototherapy device may comprise a dermatologic device that generates light energy for application to skin, e.g., for hair removal, acne treatment, tattoo removal, etc.

The operation of a phototherapy device generally involves, among other things, the generation of heat by the device. Such heat generation typically involves the production of multiple heat loads within the phototherapy device. By way of example, the phototherapy device light source produces heat. Also, the phototherapy device electronics (e.g., power supply, control circuitry, etc.) typically generates heat.

In addition, during operation a phototherapy device may be subjected to external heat loads or heat sinks that involve the transfer of heat to the phototherapy device (i.e., external heat load) or from the phototherapy device (i.e., an external heat sink). By way of example, a phototherapy device comprising a dermatologic device may receive heat due to contact with skin. In such case, the temperature of the portion of the dermatologic device that contacts the skin is less than the temperature of the portion of the skin contacted. Such a device (i.e., a device in which the temperature of the skin-contacting portion is less than the temperature of the skin portion contacted) may prove effective to cool the skin and help protect users with darker skin types. By way of further example, a dermatologic device may maintain its skin-contacting portion at a temperature that is greater than the temperature of the portion of skin contacted. In such latter case, the skin may be considered an external heat sink, while in the former case the skin may be considered an external heat load. Also, by way of further example, a phototherapy device comprising a dermatologic device may dissipate heat into the air of the room in which this device is used. In such case, the ambient conditions comprise a heat sink.

A problem associated with phototherapy devices, then, involves the control and management of heat sinks and heat loads, both internal and external to the device, including without limitation the control and management of heat transfer between one or more of such heat sinks, heat loads, and the device, to promote efficient and enhanced device operation and performance.

SUMMARY OF THE INVENTION

Particular embodiments of the present invention may reduce or eliminate problems or disadvantages associated with phototherapy device operation.

In accordance with a range of embodiments, a phototherapy device includes a light source, a light emanation block, and a heat exchanger for the dissipation of heat from device heat loads. In one embodiment, the light source comprises a source of light emitted as a result of a controlled stimulated emission. The light emanation block may include an assembly that promotes delivery of light for at least a portion of the pathway between the light source and a target area. The heat exchanger may include a first heat transfer region operatively coupled to the light source for the dissipation of heat from the light source via the first heat transfer region, and a second heat transfer region operatively coupled to the light emanation block for the dissipation of heat from the light emanation block via the second heat transfer region, wherein the first heat transfer region and the second heat transfer region are substantially thermally isolated from one another.

In accordance with a further range of embodiments, the phototherapy device may include a thermal converter and a third heat transfer region operatively coupled to the thermal converter for the dissipation of heat from the thermal converter via the third heat transfer region.

In addition, a phototherapy device thermal control method in accordance with a range of embodiments includes the steps of providing a light source that emits light as a result of a controlled stimulated emission; providing a light emanation block; and providing a heat exchanger including a first heat transfer region operatively coupled to the light source for the dissipation of heat from the light source via the first heat transfer region and a second heat transfer region operatively coupled to the light emanation block for the dissipation of heat from the light emanation block via the second heat transfer region, wherein the first heat transfer region and the second heat transfer region are substantially thermally isolated. The method according to a further range of embodiments includes the step of establishing or maintaining the first heat transfer region and the second heat transfer region at different temperatures after an emission of light from the light source.

Other technical advantages will be apparent to those of ordinary skill in the art having the benefit of the specification, drawings, and claims.

BRIEF DESCRIPTION OF THE DRAWINGS

To provide a more complete understanding of the range of embodiments of the present invention, including without limitation features and advantages thereof, reference is made to the following description, taken in conjunction with the accompanying drawings, in which.

DETAILED DESCRIPTION OF EXAMPLE EMBODIMENTS

Particular embodiments have been used to describe the invention, and a person having skill in the art and having the benefit of the included description may comprehend one or more changes, substitutions, variations, alterations, or modifications within the scope of the appended claims. The invention encompasses all such changes, substitutions, variations, alterations, and modifications.

Figure 1:
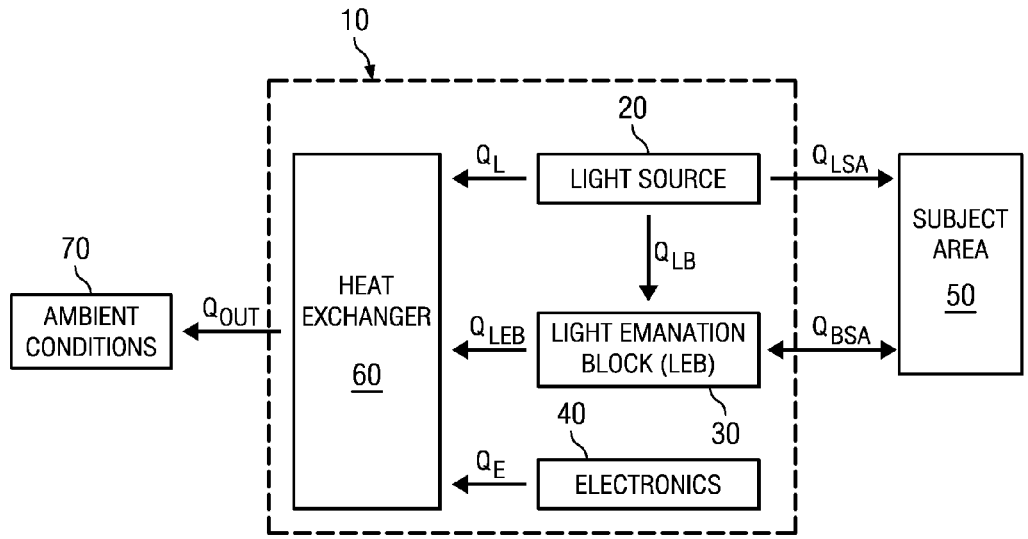
FIG. 1 illustrates in schematic form exemplary heat sinks, heat loads, and radiant energy and heat transfer paths for a phototherapy device in accordance with certain embodiments of the disclosure.

As shown in FIG. 1, phototherapy device 10 includes light source 20, light emanation block 30, electronics 40, and heat exchanger 60. The device 10 may be used in a wide variety of settings, each characterized by constant or variable ambient conditions 70 within which the device 10 operates or may be considered to operate. The device 10 also is operable for a variety of applications, each application involving a subject area 50 with which the device 10 interacts. For example, in instances where the device 10 comprises a dermatologic device, the ambient conditions 70 may comprise the conditions found in a home, clinic, hospital, outpatient treatment center, doctor's office, or other location at which a dermatologic therapy is provided involving the use of device 10. For example, air temperature generally may be regarded as 23° C. in most instances. Under such circumstances, the dermatologic therapy typically will be provided to an individual or patient over a subject area 50 comprising a portion of the person's skin.

For the sake of clarity and convenience only, the invention is described below in the context of a dermatologic device 10 for treating a portion 50 of a person's skin. However, the invention should not necessarily be understood to be so limited. For example, the apparatus and method described may have application under other circumstances that do not involve skin treatment.

Also, it is well established that heat can be transferred three ways: conduction, convection, and radiation. Unless specifically noted in the details that follow, reference to the transfer of heat refers to one or more of these ways of transfer, either alone or in combination.

Further, as used herein, the terms "light" and "electromagnetic radiation" are used interchangeably. Each term should be understood to have a broad meaning, and unless otherwise specifically noted, should not be limited only to visible light, but rather understood to encompass all wavelengths of the electromagnetic spectrum from about 300 nm (i.e., ultraviolet (UV) light) to about 15 μm (i.e., infra-red (IR) light).

The dermatologic device 10 includes light source 20. Advantageously, light source 20 comprises one or more sources of electromagnetic radiation. In accordance with a range of embodiments of the present invention, light source 20 includes one or more types of intense light sources, such as lasers, flash lamps, light-emitting diodes, laser diode bars, etc., either alone or in combination. Depending upon the embodiment, the light source 20 may provide either coherent or non-coherent light. If coherent light is provided, preferably the light is from a laser source.

Figure 2:
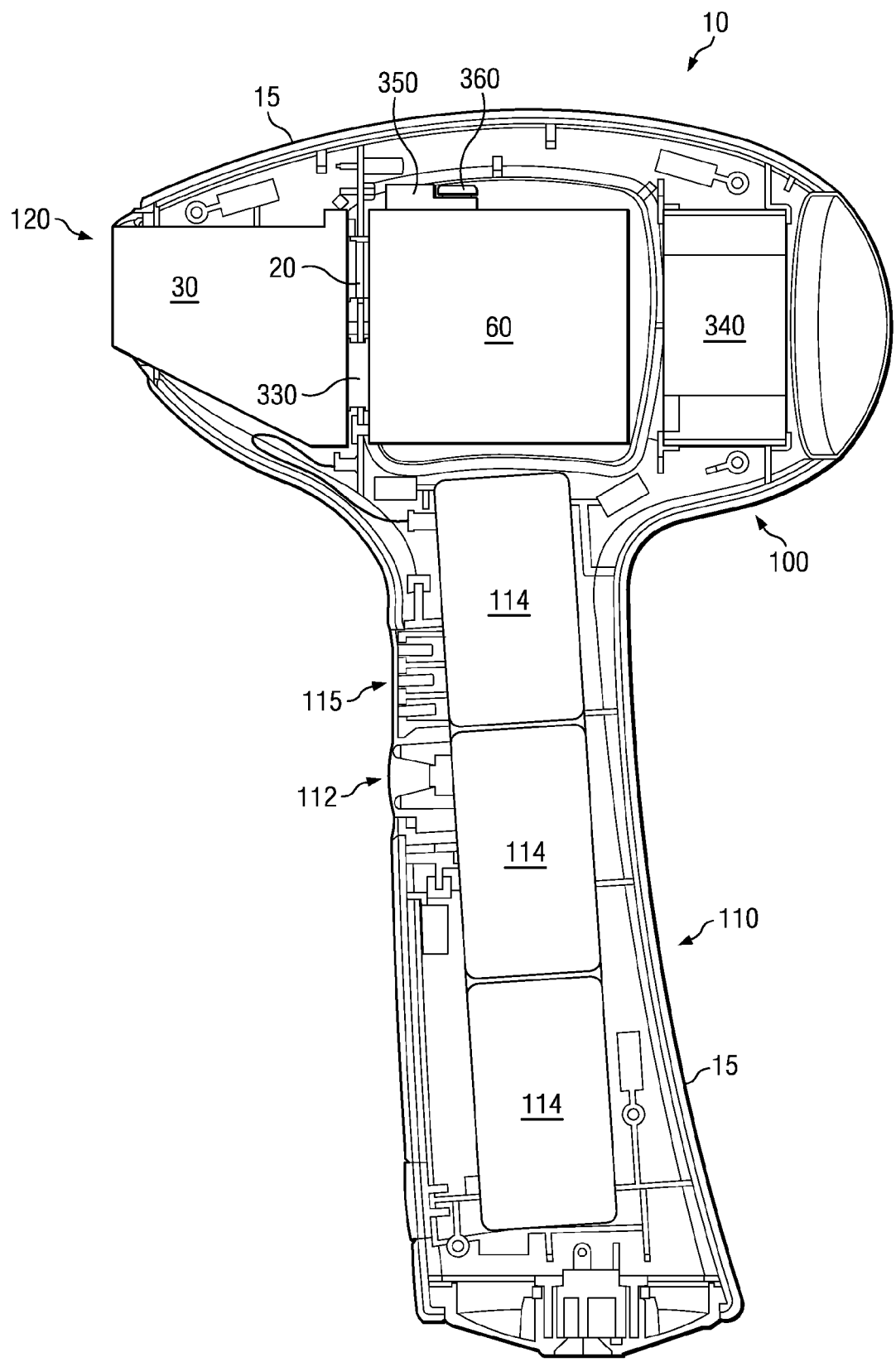
FIG. 2 illustrates in partial schematic form a cross-sectional view of an exemplary dermatologic device in accordance with certain embodiments of the disclosure.

The light source 20 may be operatively coupled to the light emanation block 30 for the delivery of a desired amount of electromagnetic radiation to the subject area 50 through an opening in the housing 15 (FIG. 2). Such delivery may be characterized in numerous ways.

For example, one measure of such delivery may be irradiance, i.e., the output power of the light source 20 divided by its area of incidence. Irradiance typically is expressed in watts per square centimeter (W/cm²). As used herein, solely for clarity and convenience, area of incidence refers to that portion of the subject area 50 upon which light from a stationary device 10 impinges during a single pulse of light. Thus, irradiance is a function of light source output power and of light beam cross-sectional area at the subject area 50. However, unless otherwise noted, and again solely for clarity and convenience, such light beam cross-sectional area shall be assumed to be circular and shall be assumed to correspond to the cross-sectional area of a circular output window of the device 10. However, the size and shape of the output window of the device 10 need not be so limited. Accordingly, for a device 10 irradiance is directly proportional to light source 20 output power and inversely proportional to the square of the output window diameter, as follows:

$$I = \frac{P}{A} = \frac{P}{\pi R^2} = \frac{4P}{\pi D^2}$$

where I is irradiance, P is output power, R is output window radius, D is output window diameter, and A is output window area.

By way of further example, the desired delivery of light to the subject area 50 may be expressed in terms of the radiant exposure of the device 10, which term is referred to herein (and commonly within industry) as "fluence" (in effect assuming a negligible contribution from scattered or retro-reflected light). Fluence typically is expressed in joules per square centimeter (J/cm$^2$). As used herein, fluence refers to irradiance multiplied by pulse duration, i.e., the duration of a single pulse of light. For a device 10 having a constant light source output power and a fixed beam area corresponding to the cross-sectional area of a circular output window of the device 10, fluence is a function of pulse duration, as follows:

$$F=It_p$$

where F is fluence, I is irradiance, and $t_p$ is pulse duration.

By way of further example, the desired delivery of light to the subject area 50 may be expressed in terms of the total energy delivered. For example, for a device 10 providing a single pulse of light, with the device 10 having a constant light source output power and a fixed beam area corresponding to the cross-sectional area of a circular output window of the device 10, total energy delivered equals fluence multiplied by output window area. Further, for such a device delivering multiple pulses of light, total energy delivered equals the product of irradiance and output window area multiplied by total pulse duration, i.e., the sum of the durations of each pulse of light.

A subject area 50 may over time "see" one or more pulses of light in a variety of ways. For example, a device 10 may deliver multiple pulses of light and be held stationary or be moved across the subject area 50; a device 10 may provide light continuously and be moved across the subject area 50; etc. Generally, in each instance the biological and other effects may be similar. A subject area 50 may see a pulse of light, for example, both as a non-pulsed (i.e., continuous wave) device moves across the subject area 50 and as a pulsed device is held stationary over the subject area 50. In certain applications, where pulses in time are close together, so that the pulses come faster than the "relaxation" period during which heat fully dissipates in the skin, the effective fluence can be close to the total of the closely spaced pulse string, and such closely spaced pulses may be considered a single pulse for the purposes of the description herein.

Further, the total time required to provide a phototherapy to a particular subject area 50 may depend upon a number of factors. For example, a subject area 50 may be greater in size than the beam area of a device 10. Under such circumstances, the device 10 must be moved across the subject area 50 (e.g., during the application of one or more light pulses), so that the total energy delivered is distributed as desired across the entire subject area 50. The total phototherapy or treatment time equals the total duration of all light pulses plus the total duration of the time between light pulses. Further, the amount of energy delivered to a particular location within subject area 50 may vary depending upon the amount of beam area overlap or gap for the light pulses. Accordingly, unless otherwise indicated, it is assumed solely for clarity and convenience that for a particular subject area 50 multiple pulses of light do not involve any overlap of, or gap between, pulse incidence areas (although methods involving overlaps and/or gaps (without limitation) are within the scope of a range of embodiments of the invention).

Where there is no substantial interruption or delay in the course of a phototherapy procedure for a particular subject area 50, device therapy rate, i.e., the rate at which the device 10 operates to provide a phototherapy, may be determined by dividing the size of subject area 50 by the time required to treat such area. Alternately, operation of the device 10 to provide a phototherapy may be characterized by a constant or variable pulse repetition frequency (PRF), i.e., the number of light pulses provided by the device per unit of time. Accordingly, in certain situations device therapy rate also may be determined by the device coverage rate, which equals the cross-sectional area of the output window of the device multiplied by the device PRF.

An example of a dermatologic device 10 in accordance with a range of embodiments of the present invention is depicted in FIG. 2. Device 10 includes a head 100 and a handle 110. The handle 110 is adapted so that a user may hold the device 10 by hand. In the example shown in FIG. 2, the handle 110 comprises a generally pistol-grip-like shape, although the invention is not limited to such form.

The handle 110 may comprise a control and may include one or more switches or buttons 112, or other input assembly, that may be activated by the user during device operation, or that may send or receive a signal, to achieve a desired function (e.g., to initiate a light pulse, to turn the device on or off, to determine whether the device 10 is proximate a subject area 50, to check device status, etc.). The handle 110 may include one or more LED indicators 115 (or other type of user interface or device output assembly or display) that convey information to a user concerning operation of the device 10 or a component thereof, concerning treatment or subject area status, etc. In the illustrated embodiment, the handle 110 also includes a compartment to hold one or more batteries 114 operable to power the device 10. Alternately, the device 10 may be adapted for use with an alternate form of internal or external power supply (e.g., a corded plug).

A mixer may be solid or hollow. For example, a hollow mixer may comprise a generally elongated tubular-shaped member with a lumen disposed therein. The mixer may increase the spatial uniformity of the light provided by light source 20 by having a mixing chamber, which may be a hollow tubular section with substantially non-absorbing side walls through which the light would propagate.

Figure 3:
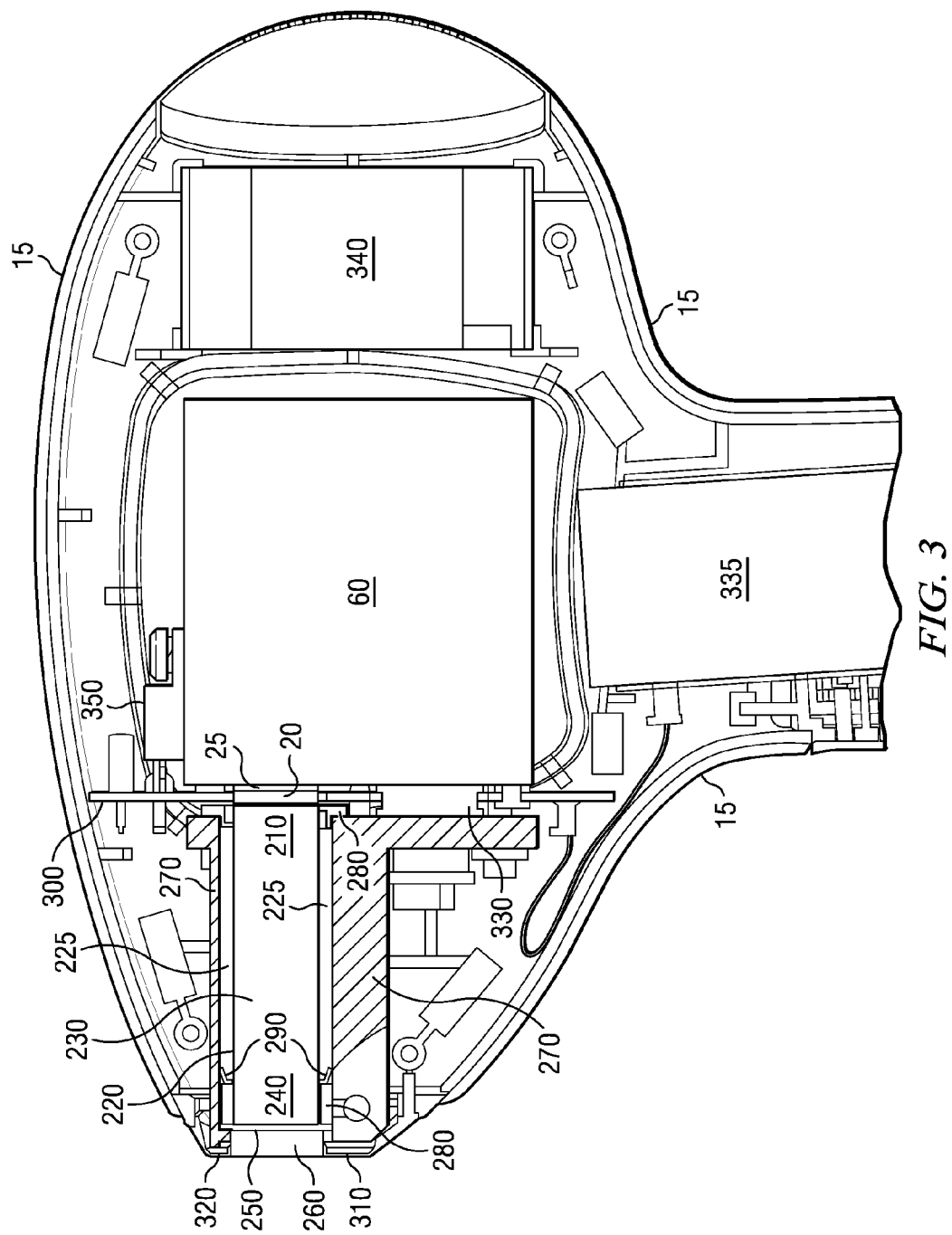
FIG. 3 illustrates in partial schematic form additional details of the exemplary dermatologic device shown in FIG. 2, in accordance with certain embodiments of the disclosure.

In an alternate embodiment, as illustrated in FIG. 3, a mixer may comprise a solid mixer 230 disposed adjacent the light source 20 and having an input face at first end 210 for receiving forward propagating light (i.e., light propagating away from the light source 20), a sidewall 220 for conveying the forward propagating light via total internal reflection (TIR), and an output face at second end 240 for transmitting the forward propagating light. The solid mixer 230 may have sidewalls that are flat planes and that are parallel to the optical axis. The input and output faces may be polygonally shaped (e.g., triangular, rectangular, hexagonal, octagonal), although other free-form or curved shapes also may be used, and the input and output faces need not have the same shape. The solid mixer 230 (which may be termed a "mixer") may be made of a solid, elongated block of transparent material (e.g. boro-silica glass, acrylic, sapphire, etc.) and may be disposed in an elongated cavity 225. Solid mixer 230 may include a polygonal shaped input face positioned at first end 210 proximate laser diodes of a light source 20, and a circular shaped output face at second end 240, with a sidewall 220 extending there between and having a cross-sectional shape that gradually changes (e.g., from rectangular to circular). The gradual change in cross-sectional shape is such that light traveling along the solid mixer 230 may be reflected with little or no loss by total internal reflection (TIR), and absorption of light at the lightguide sidewall is minimized.

A solid acrylic solid mixer 230 using TIR to reflect the light along the lightguide is one form of a mixer. Another form of mixer is a hollow mixer relying on surface reflections. However, the invention is not necessarily limited to only such approaches to light propagation.

For example, although the shape of a lightguide may be such that a generally rectangular distribution of the light output from light source 20 is transformed to a generally circular distribution, the lightguide need not have a rectangular input face and a circular output face. Also, by way of further example, in accordance with one range of embodiments, portions of the lightguide sidewall may remain substantially parallel along the axis of travel of light, and the input face proximate the light source 20 may diverge up to about seven degrees from the plane normal to the optical axis, so that no substantial leakage of light occurs out of the sidewall; but again, the invention is not necessarily so limited, and the circumstances involved in a particular application may impact the configuration used (e.g., sidewall and input and output face divergence may vary depending upon the index of refraction of the lightguide materials used).

In accordance with a range of embodiments of the invention, the lightguide sidewall may be tapered. For instance, the lightguide input face may have a different desired cross-sectional area and/or shape as compared to the lightguide output face. Generally, the higher the refractive index of material used to form the lightguide, the greater the amount of taper or input/output face divergence that may be implemented, e.g., so that substantial light leakage out of the lightguide does not occur. That is, light rays preferably strike the sidewall above the critical angle (measured off the normal to the sidewall) for total internal reflection.

In alternate embodiments of a mixer, the mixer input and/or output faces may include diffusers, e.g., by including a diffusive material on one or more of these faces. If the input and/or output faces produce a sufficient amount of diffusion for the light, a separate diffuser end 240 may not be required for some embodiments. The inclusion of one or more diffusers on one or more of such faces may increase the leakage of light via the side walls. Alternately, a diffuser separate from the lightguide (e.g., one adjacent to or spaced from an end of the lightguide) may be used.

As used herein, the terms "over" and "on" both inclusively include "directly on" (no intermediate materials, elements or space disposed there between) and "indirectly on" (intermediate materials, elements or space disposed there between). Likewise, the term "adjacent" includes "directly adjacent" (no intermediate materials, elements or space disposed there between) and "indirectly adjacent" (intermediate materials, elements or space disposed there between).

In accordance with one range of embodiments, a mixer serves to mix the light emitted from laser diode bars of a light source 20 including two GaAlAs laser-diode-bar arrays emitting at approximately 800-820 nm, to produce a generally spatially uniform beam profile at the output window of the device 10. The length of the mixer preferably is designed to provide substantial spatial uniformity of light on a one square centimeter output window from two diode bars spaced about 6 mm apart.

In one embodiment, a barrel 270 may provide a low thermal resistance path between the device output window and a heat-removal element. To reduce light absorption (e.g., from back-reflected or back-scattered light), the barrel 270 may comprise a hollow chamber within which a mixer is at least partially disposed, and the walls of the barrel proximate the mixer may be either polished, coated, or otherwise adapted to achieve high reflectivity of light. The barrel wall material may be any material with good thermal transfer properties (e.g., copper, aluminum). The wall thickness of the mixer may provide good thermal conductivity between the output window and heat removal element. For aluminum walls surrounding a one square centimeter output window, for example, a wall thickness of about 2 mm may be required to conduct about 8 W of average power to a thermal source 2 cm away with a 5° C. temperature rise. The volume and weight of the barrel may be about 4 $cm^3$ and 3.5 g. The thermal load on the barrel due to light absorption may be less than 4 W.

An alternate embodiment of a barrel may include various shapes and may comprise multiple elements to achieve the thermal link between the output window and the heat removal element and to achieve low light absorption. The cross-sectional shape of the barrel, or its elements, may be any of a variety of shapes (circular, oval, hexagonal, rectangular, octagonal, etc.) and may vary or not vary along the length of the barrel. Because the skin, or the diffuser, or the walls of the mixer may remit light in a direction away from the skin, the barrel may comprise low-absorbing side walls and/or a low-absorbing surface opposite the output aperture. Such low-absorbing surface may contain one or more openings through which light from the light source passes, or may simply constitute the surface adjacent to the light source.

In an alternate embodiment, a mixer may comprise at least a portion of the barrel, which may comprise an inner housing or surface, such as a sheet of polished metal, for the purpose of reflecting light from the light source toward the output window; and a thicker metal outer housing or surface, such as a copper or aluminum assembly, to conduct heat from the output window to a heat-removal element. In this embodiment, the inner housing may alternatively be fabricated from a solid transparent material such as glass or acrylic, and the light from the light source may be reflected toward the output window by total internal reflection within the glass or acrylic material.

The channeled light exits the mixer (e.g., solid mixer 230) and preferably passes through a diffuser 250 and a window 260 to impinge upon a subject area 50. The diffuser 250 may comprise an optical diffuser that is transmissive or reflective. As used herein, the term "transmissive diffuser" is intended to describe an element incorporated into a light path having an input surface which the light initially strikes; and a second, output surface from which light propagates. Such input and output surfaces of the transmissive diffuser are separated by the material of the diffuser itself. Further, as used herein, the term "reflective diffuser" is intended to describe an element incorporated into a light path having a first or input surface which the light initially strikes; however, in contrast to a transmissive diffuser, this first surface also serves as the output surface from which light propagates from the diffuser. Further, the term "reflective" is used in this context to include remitted light. That is, the diffuser may scatter or refract light as well.

The diffuser may increase the divergence of the light emitted from light source 20 and reduce the spatial coherence of the light source. The diffuser may be made of a material that scatters light traveling through it, such as an opalized glass substrate. The diffuser may comprise an optical diffuser to scatter the light to make it conform to eye safety standards.

The applicator tip of the device 10 may comprise a transparent, high heat capacity and high thermal diffusivity material, such as sapphire, with a low thermal resistance connection to the barrel. For example, an output window thickness of 5 mm may provide an acceptable heat sinking capability for a one square centimeter sapphire window. The volume and weight of the output window may be about 0.5 $cm^3$ and about 2 g, respectively. The thermal load on the output window may be about 8-9 W of average power.

The applicator tip may be pressed or held against or proximate to the surface of the skin to be treated. The applicator tip preferably comprises a window made of sapphire in contact with the skin, because of its relatively high thermal conductivity. The applicator tip, however, may include an opening or aperture such that the applicator tip component that contacts the person's skin may include a frame of an opening.

In accordance with a range of embodiments, the applicator tip preferably may include a bacteria-resistant or an anti-microbial substance to help reduce the spread of bacteria or microbes across a subject area, e.g., due to movement of the device during use. For example, and without limitation, an applicator tip may include an impregnated layer or surface coating of titanium dioxide.

The mixer (e.g., solid mixer 230), diffuser 250, and window 260 are operatively coupled to form in part a light emanation block 30. The light emanation block 30 also may include the barrel 270. The mixer (e.g., solid mixer 230), diffuser 250, and window 260 may be secured within the barrel 270 by one or more collars 280 and fastening rings 290, or other such suitable fastening devices. One or more of the fastening devices 280 and 290 may serve to align one or more of the light emanation block components relative to the others, to create a continuous light pathway from light source 20 through at least a portion of the applicator tip, e.g., window 260 illustrated in FIG. 3.

Figure 4:
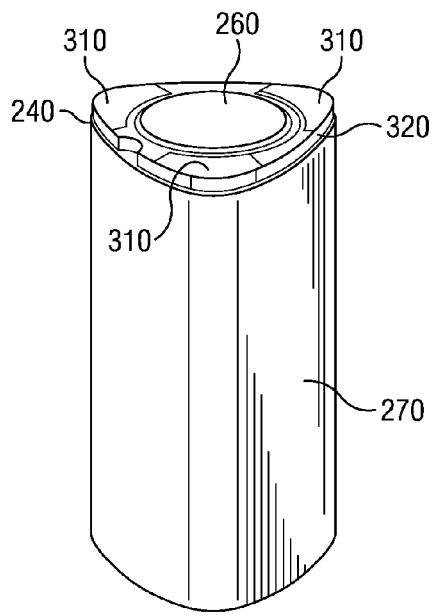
FIG. 4 further illustrates in perspective view additional details of a portion of the exemplary dermatologic device shown in FIG. 3, in accordance with certain embodiments of the disclosure.

As shown in FIG. 3, the head 100 of device 10 may further include one or more circuit boards 300, 320; a heat exchanger 60; a thermoelectric (TE) module 330; and a fan 340. An outer housing 15 may enclose one or more of the various components of device 10. The first circuit board 320 may be operatively coupled within the head 100 at the applicator tip proximate the window 260. The board 320 may include capacitive sensors 310 for use in detecting the presence of skin or other subject area 50 proximate the window 260. See also FIG. 4, which in addition illustrates further an exemplary end 240 of barrel 270. One or more mechanical sensors or switches also may used, either alone or in combination with capacitive sensors, for detection purposes.

A dermatologic device 10 in accordance with a range of embodiments of the invention may generate a light pulse automatically when the applicator tip 120 of device 10 is placed or held against or proximate to an individual's skin. Skin contact may be sensed using the capacitive sensors 310 that detect a capacitance change resulting from skin proximity or contact, or sensed using mechanical sensors or switches. An information or control signal may be generated at board 320 and communicated to board 300 for initiation of a light pulse, e.g., in response to initial skin contact, to maintaining such contact, etc. In addition, an audible tone, light, or other perceptible alarm or indicator may be used to identify when skin proximity or contact by the applicator tip 120 (or other desired condition or parameter for the device 10) is achieved.

The circuit board 300 preferably is disposed proximate the first end 210 of the mixer 230, and includes control circuitry, memory, and other electronic components generally needed for the operation of device 10 (although electronic components may be disposed in other locations within device 10 as well). The board 300 preferably is operably coupled to the power supply 335, which may include one or more batteries; light source 20; and to one or more buttons or switches 112 (or another form of device input or user interface), to enable users to turn the device on and off, to initiate a light pulse, to reset or cancel an alarm, to provide or retrieve information (e.g., about the device or the therapy), to change operational settings, or to perform other tasks. The board 300 also preferably is operably coupled to and controls the operation of a cooling fan 340 oriented to provide ambient air to or across at least a portion of heat exchanger 60.

Figure 5:
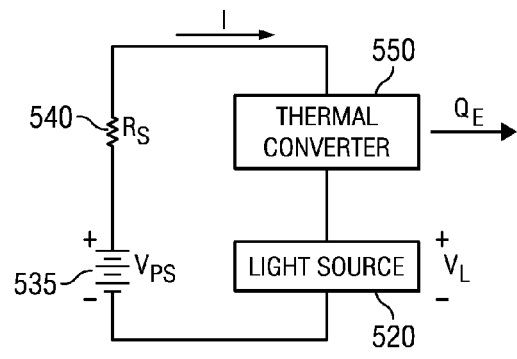
FIG. 5 illustrates a circuit diagram modeling in part the exemplary dermatologic device shown in FIG. 2, in accordance with certain embodiments of the disclosure.

During the operation of device 10, the board 300 (and its associated electronic circuitry components) acts or may be considered to act as a heat load for the device 10. As shown in FIG. 5, in accordance with certain embodiments, the electronic circuitry of the device 10, which preferably includes a direct drive circuit architecture using a field effect transistor (FET) to control current (although an indirect approach using, e.g., a buck-boost converter architecture also may be used), may be modeled as a single loop circuit with the following components connected as shown: a power supply 535; a resistor 540 having a resistance value Rs; thermal converter 550; and light source 520. A voltage $V_{PS}$ is provided by the power supply 535. The voltage drop $V_L$ across the light source 520 depends upon the type and/or number of the light sources used. For example, use of a single laser diode bar may result in a voltage drop $V_L$ of approximately two volts (2V), whereas use of two such laser diode bars may result in a voltage drop $V_L$ of four volts (4V). The resistor 540 substantially models the parasitic resistance $R_S$ of at least a portion of the electronic components of device 10. The resistance $R_S$ typically is substantially constant for a particular configuration of device 10. For example, the resistance $R_S$ may be in the range of about eight to about fifty milliohms (8-50 mΩ) for a device 10 as generally described herein. Accordingly, the voltage drop across the resistor 540 may be determined using the loop current (I) and the resistance value ($R_S$) and Ohm's law.

The thermal converter 550 preferably models a FET thermal converter that uses FETs as a controlled impedance to enable control of dissipated power proportional to the product of the FET's drain-to-source voltage and source current. The resulting heat load, designated $Q_E$, is identified by the resulting thermal converter temperature increase and is directly proportional to the time-averaged internally dissipated power. Generally, the efficiency of FET thermal converters remains substantially the same over a wide range of operating temperatures. With reference to the parameters shown in FIG. 5, some examples of representative values are set forth in Table 1 for an exemplary dermatologic device 10 in accordance with certain embodiments of the present disclosure, where the numerical values shown are estimated or approximate amounts.

TABLE 1

|  | Example A | Example B |
| --- | --- | --- |
| Power Supply | 5 cell NiMH | 1 cell LiFePO$_4$ |
| $V_{PS}$ | 5.75 V-6.75 V | 2.9 V-3.4 V |
| $R_S$ | 40 mΩ | 8 mΩ |
| I | 40 A | 50 A |
| Thermal Converter | FET | FET |
| Light Source | 2 laser diode bars | 1 laser diode bar |
| $V_L$ | 3.8 V | 1.9 V |
| $Q_E$ | 40 W (peak power) 10 W (average 25% duty factor) | 40 W (peak power) 10 W (average 25% duty factor) |

As shown in FIGS. 1 and 3, the generation of light by light source 20 results in a radiant energy transfer $Q_{LSA}$ to subject area 50. At the same time, the interaction of the produced light with the light emanation block 30 (e.g., the barrel 270, mixer 230, diffuser 250, and window 260) results in an energy transfer $Q_{LB}$ to the light emanation block 30. In one embodiment, heat is transferred from diffuser 250 and window 260 to barrel 270. Barrel 270 preferably dissipates heat via a heat transfer $Q_{LEB}$.

The applicator tip 120 of device 10, including window 260, may contact subject area 50 during use. Where the subject area 50 is a portion of an individual's skin, the subject area 50 may be considered absent therapy to have a substantially constant temperature that is about normal skin temperature. In accordance with a range of embodiments, the temperature of one or more portions of tip 120 may be monitored and/or adjustable. In accordance with one range of embodiments, at least a first portion of tip 120 may be maintained in whole or in part at or above normal skin temperature. In accordance with a range of embodiments such temperatures may be maintained in whole or in part at or above normal skin temperature during therapy. To the extent that any such first tip portion is so maintained, a heat flow $Q_{BSA}$ from the light emanation block 30 to the subject area 50 may occur. Such a heat flow may be identified, for example, by a part of the head 100 contacting the skin feeling warm to the touch, or by the device performing a pre-therapy, concurrent, or post-therapy heating procedure for at least a portion of the skin or targeted subject area 50. Also, at least a second portion of tip 120 may be maintained in whole or in part at or below normal skin temperature. To the extent that any such second tip portion is so maintained, a heat flow $Q_{BSA}$ to the light emanation block 30 from the subject area 50 may occur. Such a heat flow may be identified, for example, by a part of the head 100 contacting the skin feeling cool to the touch, or by the device performing a pre-therapy, concurrent, or post-therapy cooling procedure for at least a portion of the skin or targeted subject area 50. Accordingly, the heat flow $Q_{BSA}$ is represented in FIG. 1 as a double-sided arrow, as the direction of net heat transfer may vary and typically will depend upon the circumstances involved in a particular application.

As shown in FIGS. 1-3, the device 10 includes a heat exchanger 60. The heat exchanger 60 may be operatively coupled to the driver circuit board 300, to the light source 20, and to the light emanation block 30. The heat exchanger 60 also may be operatively coupled to barrel 270 of light emanation block 30 via thermoelectric (TE) module 330; to driver circuit board 300 via thermal converter 350; and to light source 20 via an electrical insulator 25 having relatively high thermal conductivity. Such assembly results in heat exchanger 60 promoting dissipation of the heat loads of light source 20, light emanation block 30, and electronics 40 (such dissipation shown in FIG. 1 by the transfers $Q_L$, $Q_{LEB}$, and $Q_E$, respectively).

Figure 6:
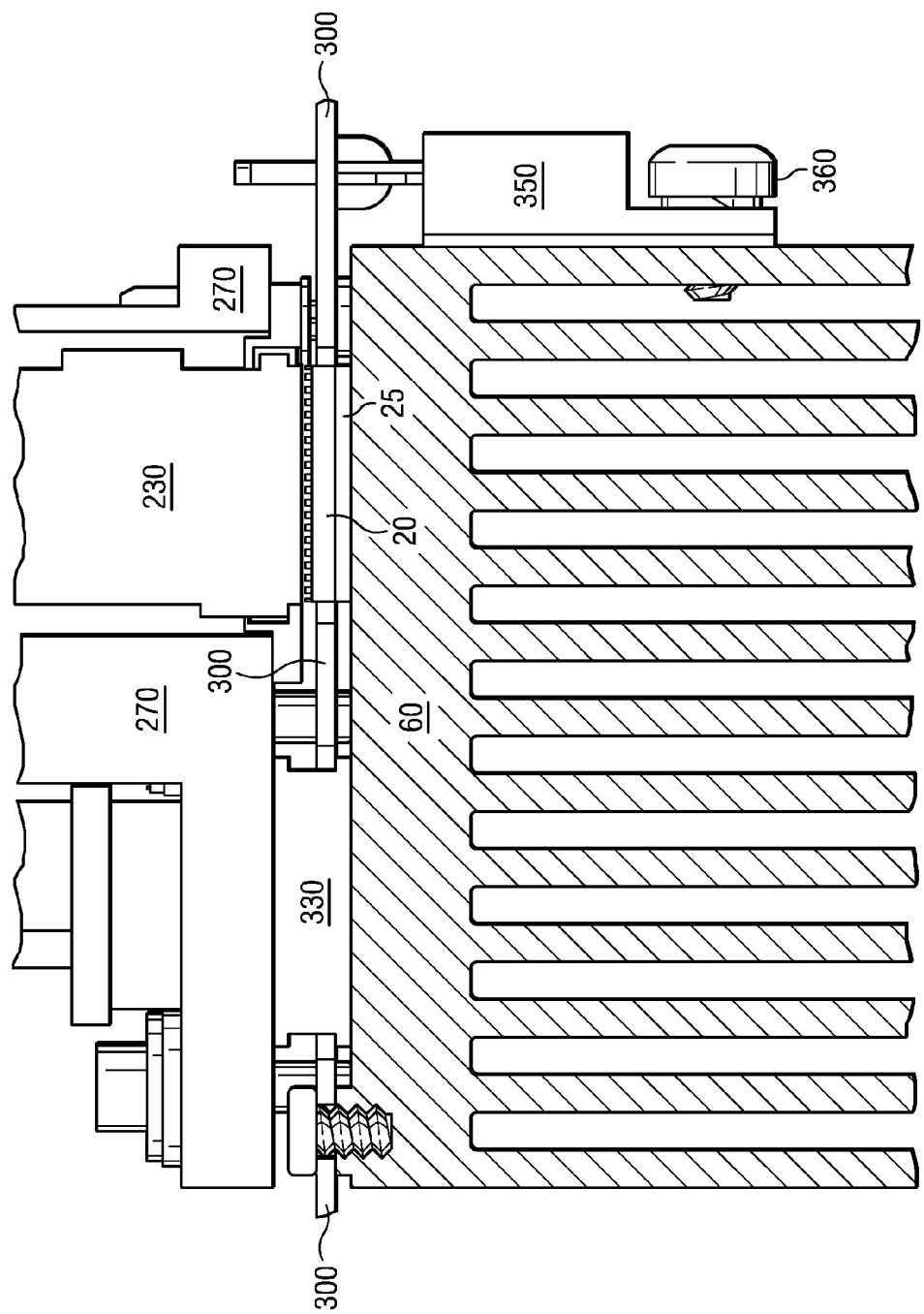
FIG. 6 further illustrates in partial schematic form additional details of an exemplary configuration of a portion of the exemplary dermatologic device shown in FIG. 3, in accordance with certain embodiments of the disclosure.

In accordance with one range of embodiments, the heat transfer $Q_E$ occurs as a result of the thermal coupling of thermal converter 350 and heat exchanger 60. Such coupling may permit, for example, the direct or indirect transfer of heat between converter 350 and heat exchanger 60. As shown in FIG. 6, a screw 360 or other suitable heat transfer medium operatively couples converter 350 and heat exchanger 60. In accordance with a range of embodiments of the invention, battery chemical potential or other measure or representation of power supply is substantially matched to a laser diode bar package, in effect (among other things) substantially limiting the amount of heat that may be dissipated into the heat exchanger 60. Voltage matching may occur, for example, when the voltage of the power supply ($V_{PS}$) is equal to the sum of the forward voltage of the laser diode bar and the voltages developed across the parasitic series resistance of all the other circuit components. In accordance with a range of embodiments, voltage matching may be achieved in whole or in part by adjusting the resistance of one or more components (e.g., FET, current sense resistor, PCB traces, battery parasitic resistance). Additionally, the nominal voltage developed across the other circuit components can be chosen by tuning the drive current of the laser diode bar by varying the number of laser diodes in the bar or by adjusting the size of the laser diodes in the bar as desired or required.

Figure 11:
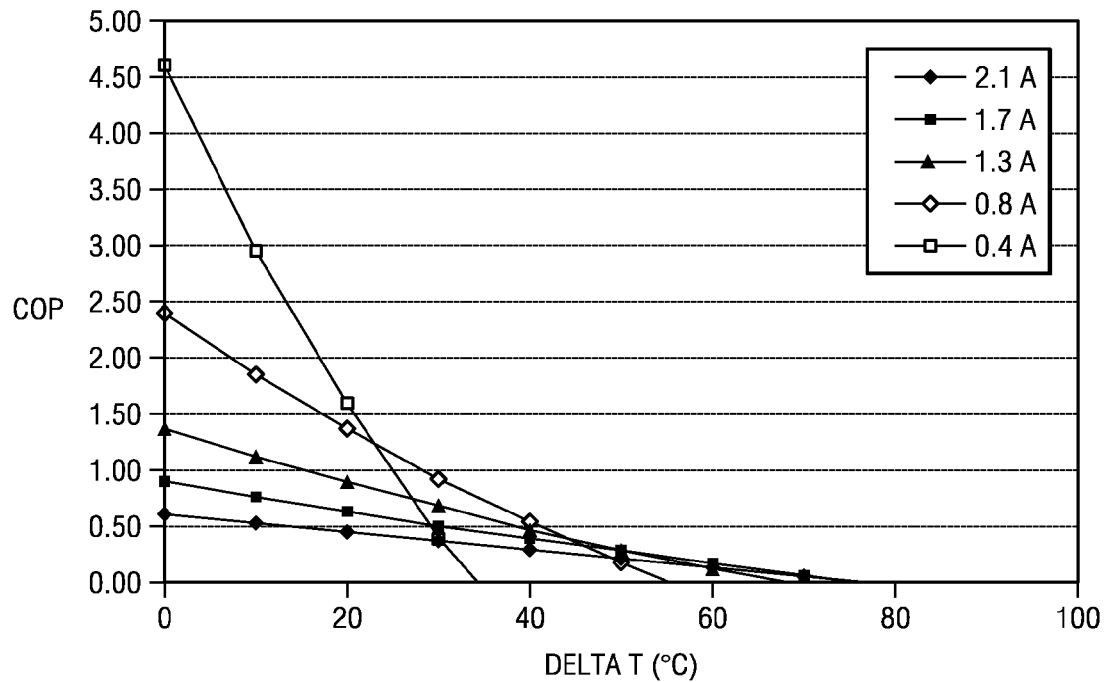
FIG. 11 is a graph illustrating for an exemplary thermoelectric module that may be used in accordance with certain embodiments of the disclosure, the coefficient of performance of the module as a function of temperature difference across the module, parameterized by current in the thermoelectric module.

The heat transfer $Q_{LEB}$ occurs as a result of the thermal coupling of light emanation block 30 and heat exchanger 60. Such coupling may permit, for example, the direct or indirect transfer of heat between light emanation block 30 and heat exchanger 60. For example, as shown in FIGS. 3 and 6, a TE module 330 may be used to transfer heat indirectly between barrel 270 and heat exchanger 60. One example of a TE module 330 that may be used is the CP0.8-63-06 Thermoelectric Cooler (Metcor Corporation, Trenton, N.J.). FIG. 11 generally shows certain exemplary performance data for such a module, i.e., coefficient of performance (COP) as a function of temperature difference (DELTA T (° C.)) across the module, for various applied currents.

The heat transfer $Q_L$ occurs as a result of the thermal coupling of light source 20 and heat exchanger 60. Such coupling may permit, for example, the direct or indirect transfer of heat between light source 20 and heat exchanger 60. For example, as shown in FIGS. 3 and 6, light source 20 may include one or more laser diode bars thermally coupled to heat exchanger 60.

Figure 12:
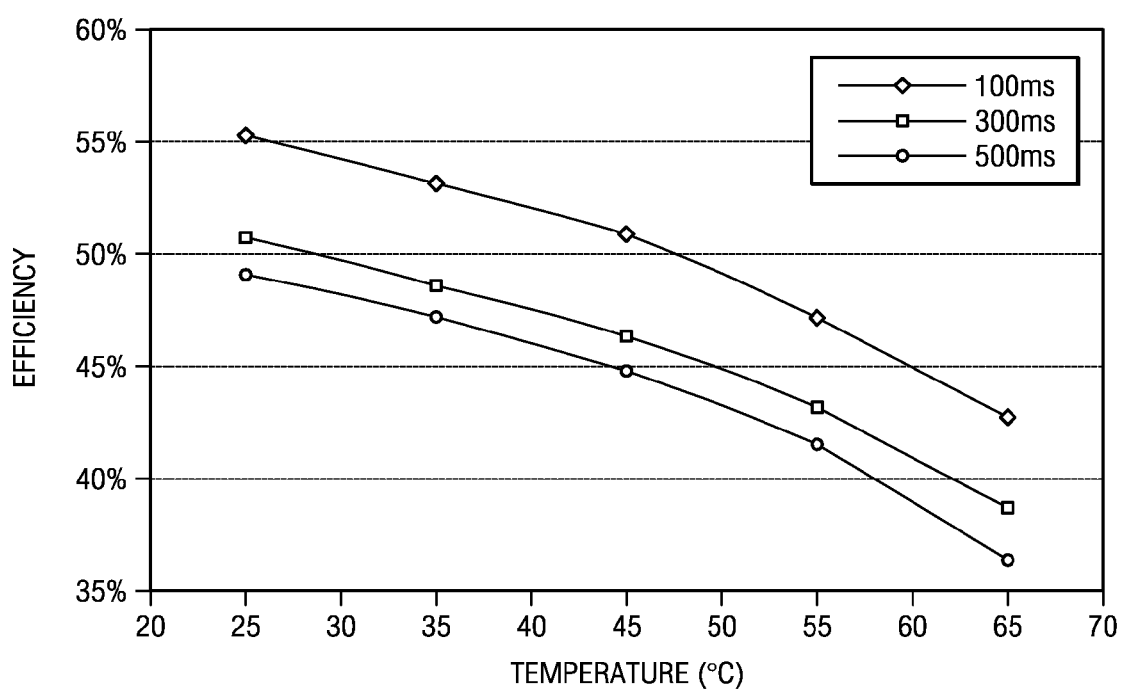
FIG. 12 is a graph illustrating for an exemplary laser diode bar that may be used in accordance with certain embodiments of the disclosure, the efficiency of the laser diode bar as a function of its operating temperature, parameterized by pulse duration.

In accordance with a range of embodiments of the present invention, the laser diode bars may operate at a wide range of temperatures. For example, and without limitation, laser diode bar operating temperatures may be different than the laser diode bar operating temperatures found in prior art phototherapy devices. As laser diode bar operating temperature increases, for example, the efficiency of the laser diode bar generally decreases. See, for example, FIG. 12, which shows such relationship for a particular exemplary device configuration, parameterized by pulse duration.

Laser diode bar efficiency may be considered a function of the laser diode bar operating temperature. Thus, the efficiency and performance of the device 10 may be controlled by controlling laser diode bar operating temperature. In accordance with a range of embodiments of the present invention, laser diode bar operating temperature, and hence laser diode bar efficiency, may be controlled by regulating heat dissipation for the device 10.

By way of example, for a laser diode based phototherapy device 10, light source efficiency may under certain conditions drop off at about one percent (1%) per degree celsius (° C.) of light source operating temperature increase. That is, a 10° C. temperature increase may generally result in a 10% efficiency reduction. Further, the incremental heat produced by laser diode bars due to an increase in operating temperature typically is approximately directly proportional to their operating temperature rise. The ability to dissipate heat due to a laser diode bar operating temperature increase typically increases at a rate greater than the rate of incremental heat production associated with the temperature rise. For example, a laser diode bar operating temperature increase of 10° C. may produce 10% more heat, but the rate of heat dissipation for the device 10 may increase by about 50%. Other embodiments may have different temperature sensitivities. Thus, in accordance with a range of embodiments of the present invention, the performance of device 10 may be enhanced by a device therapy rate or coverage rate increase based upon control of laser diode bar operating temperature. Such control may be achieved, for example, through regulation of heat exchanger temperature or of the one or more other thermal factors described herein.

Laser diode bar operating temperature typically may depend upon the average temperature in heat exchanger 60 and upon the magnitude of the temperature rise that occurs as a result of a light pulse. For example, in a situation where a relatively constant 40 amp (40 A) current is repeatedly driven through a laser diode bar to produce a series of light pulses, a heat exchanger thermally coupled to the laser diode bar may have an average temperature during device operation of about 42° C., but the current pulse to cause a light pulse may cause the laser diode bar operating temperature to temporarily rise to about 62° C. during the current pulse.

Generally, laser diode bar operating temperatures may vary in ranges up to an average operating temperature of about 75° C. Above that level (i.e., 75° C.), many laser diode bars stop lasing completely. In prior art devices, average operating temperatures above about 42° C. generally are not achievable. In contrast, in accordance with the present invention operating temperature ranges above such a limit are preferred, e.g., an average operating temperature in the range of about 42° C. to about 75° C., and more particularly at about 55° C. or 60° C., depending upon efficiency, temperature sensitivity, and the amount of heat that may be transferred from the heat exchanger to ambient conditions. For example, if a first laser diode bar operated at 61° C. has twice the difference in temperature ($\Delta T=38°$ C.) compared to ambient (23° C.) as a second laser diode bar operated at 42° C. ($\Delta T=19°$ C.) and, therefore, may reject twice as much heat as the second laser diode bar. Although the laser diode bar at 61° C. may operate less efficiently (e.g., require more current per unit light produced), the enhanced ability to shed heat may improve overall performance under some conditions. For example, operating at higher temperature may allow more light pulses per unit time.

Accordingly, where laser diode bar operating temperature may be considered as depending upon the average heat exchanger temperature and the magnitude of the temperature rise due to a current pulse to cause a light pulse, concerns for increased laser diode bar efficiency suggest a need to keep both the heat exchanger temperature and the light pulse temperature rise relatively low. However, in accordance with a range of embodiments of the invention, device 10 efficiency and performance may be enhanced by controlling heat exchanger temperature and/or light pulse temperature spikes, so that laser diode bar efficiency decreases and/or heat exchanger temperature increases, which in part results in increased heat dissipation from device 10.

The heat exchanger 60 preferably is a fin-type heat exchanger. The heat exchanger 60 may be formed of one or more metals (e.g., steel, Al, Cu) or other thermally conductive materials. Preferably, the heat exchanger 60 is formed in a shape, and is made of such thermally conductive materials, to provide effective thermal dissipation of one or more of the heat loads associated with the heat transfers $Q_L$, $Q_{LEB}$, and $Q_E$. To promote such thermal dissipation, the heat exchanger 60 may be used in conjunction with one or more components, included within or external to the heat exchanger, to help promote heat dissipation from exchanger 60 to ambient conditions, i.e., the heat transfer $Q_{OUT}$ as shown for example in FIG. 1. For example, as shown in FIGS. 2 and 3, a fan 340 may be used to direct ambient air across at least a portion of the fins of heat exchanger 60 to promote cooling. One or more other heat dissipation components also may be used, either alone or in combination with a fan.

For clarity and convenience, the heat exchanger 60 is shown in FIGS. 1, 2, and 3 in schematic form. However, the heat exchanger 60 need not be nor act as a single heat transfer device serving all heat loads of device 10. For example, and without limitation, the heat exchanger 60 may comprise one or more thermal transfer assemblies independently associated with one or more of the heat transfers $Q_L$, $Q_{LEB}$, and $Q_E$. Each such thermal assembly may have a separately identifiable pathway for at least a portion of the dissipation of heat from the device 10 to ambient, and each assembly may include one or more internal or external components to help promote heat dissipation.

According to one range of embodiments of the invention, the heat exchanger 60 may comprise multiple separate heat exchangers. For example, a first heat exchanger may be thermally coupled to light source 20, a second may be thermally coupled to light emanation block 30, and a third may be thermally coupled to electronics 40.

Figure 7A:
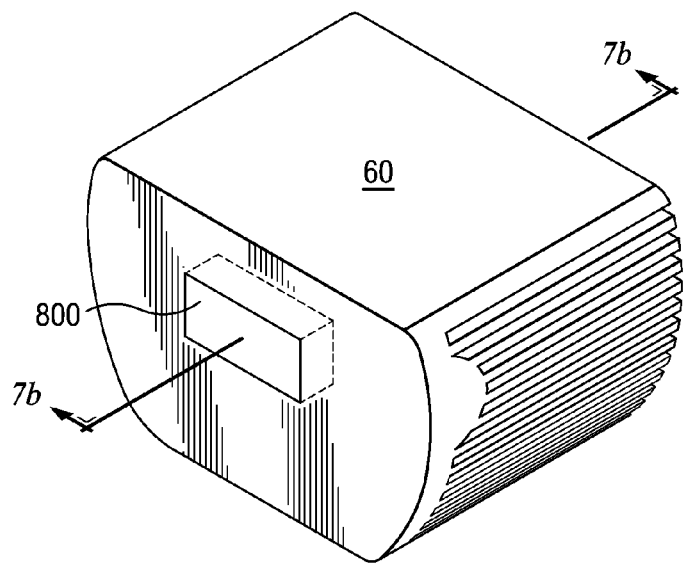
FIG. 7a illustrates in perspective view an exemplary heat exchanger, in accordance with certain embodiments of the disclosure.
Figure 7B:
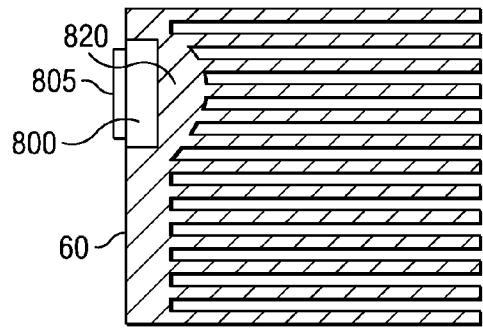
FIG. 7b illustrates a cross sectional view along line 7b-7b of the heat exchanger shown in FIG. 7a, in accordance with certain embodiments of the disclosure.
Figure 8A:
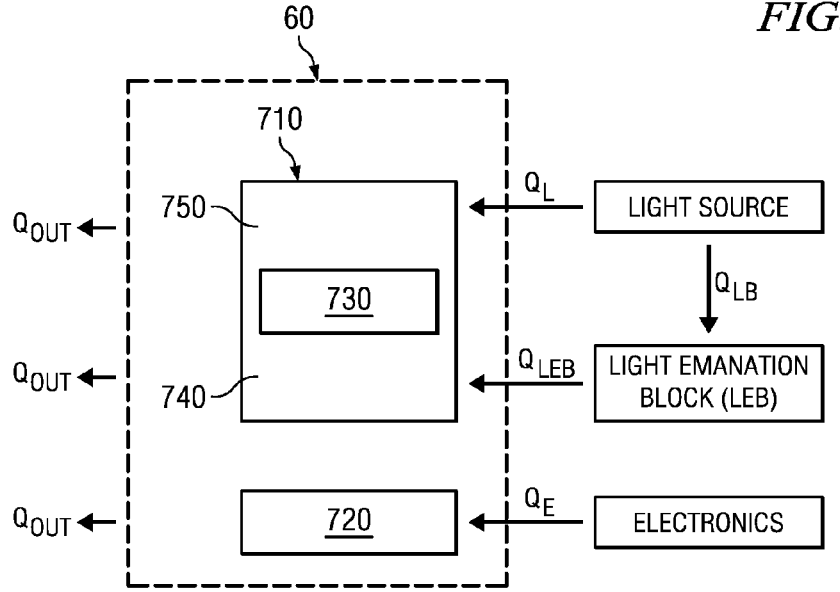
FIG. 8a illustrates in schematic form a heat exchanger and its associated radiant energy and heat transfer paths, in accordance with certain embodiments of the disclosure.
Figure 8B:
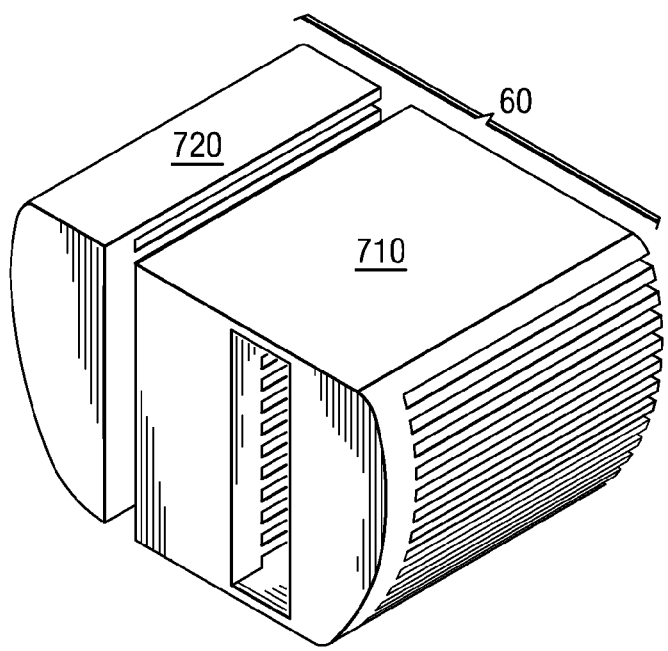
FIG. 8b illustrates in perspective view an exemplary heat exchanger as shown in FIG. 8a, in accordance with certain embodiments of the disclosure.
Figure 8C:
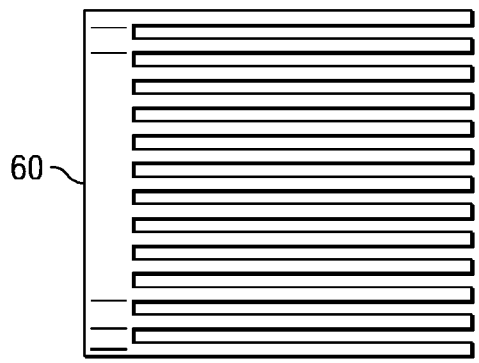
FIG. 8c illustrates a side view of the heat exchanger shown in FIG. 8b, in accordance with certain embodiments of the disclosure.
Figure 8D:
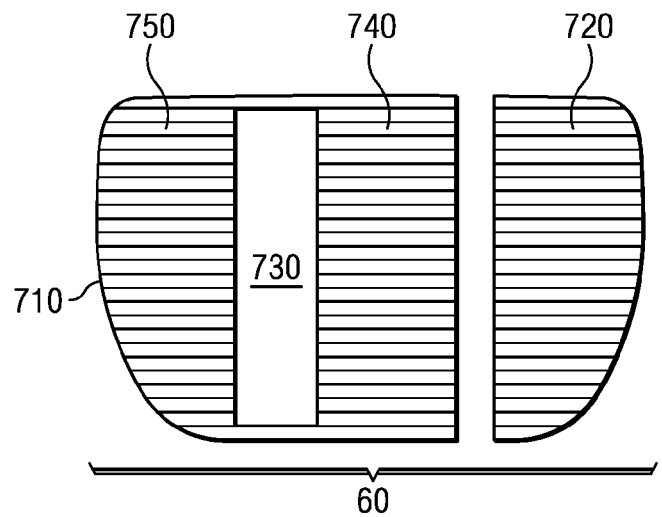
FIG. 8d illustrates an end view of the heat exchanger shown in FIG. 8b, in accordance with certain embodiments of the disclosure.

The heat exchanger 60, in accordance with one range of embodiments of the invention, may be of a variety of types, shapes, and sizes. For example, for a particular application of the present invention, it may be advantageous to provide a heat exchanger 60 that is a finned heat exchanger, wherein proximate to at least one associated heat load a first heat exchanger portion is provided having a relatively large or increased heat capacity as compared to a second heat exchanger portion. As shown in FIGS. 7a and 7b, such first portion may include one or more of the following: an insert 800, wherein the insert 800 is formed to have a higher heat capacity than a second portion of the heat exchanger 60; and a "bump" or raised segment 820, wherein the bump 820 comprises a relatively large volume of material as compared to a second portion of the heat exchanger 60. Typically, average heat exchanger temperature primarily depends upon and is a function of total fin area. Increasing local heat capacity near the diode bar package 805 by providing bump 820 generally results in a reduction of fin area. Related to the insert 800, heat capacity in the exchanger may be adjusted, for example, through the use of alternate materials (e.g., copper, aluminum) either in addition to or in replacement of the materials of the type that may be used in heat exchanger construction (e.g., steel).

As one aspect of certain embodiments of the invention, a balance may be achieved for a particular application between average heat exchanger temperature (which typically will increase as heat capacity near the diode bar package increases, primarily due to a loss of fin surface area) and current pulse temperature rise (which typically will decrease as a result of an increase in heat capacity near the diode bar package) to provide a desired level of device operational efficiency and performance in that particular application. Raising the operating temperature of the diode bar package permits an increase in the temperature difference between the heat exchanger temperature and ambient conditions, resulting in enhanced or optimized cooling being available from the heat exchanger. Thus, in some embodiments, an aspect of the invention may be to balance the gains due to increased heat transfer efficiency associated with an increased diode bar package or heat exchanger temperature with diode package efficiency losses also associated with the increased diode bar package or heat exchanger temperature.

In accordance with a range of embodiments, the heat exchanger 60 also may be adapted to be an assembly of n heat exchange elements that substantially thermally operate as at least n+1 heat exchangers, where n is a positive integer. At least one heat exchange element may include two or more heat transfer portions substantially thermally isolated from one another, with the portions at least serving to dissipate heat from separate heat loads associated with device 10. For example, and without limitation, as shown in FIGS. 8a-d, heat exchanger 60 includes a first heat exchange element 710 and a second heat exchange element 720. Exchange element 710 includes a thermal isolator 730 that substantially inhibits the transfer of heat between a first portion 740 of element 710 and a second portion 750 of element 710. The isolator 730 may comprise a divide or slot in which air acts as a thermal inhibitor. Alternately, one or more insert materials of low thermal conductivity may be used for isolator 730.

Figure 10A:
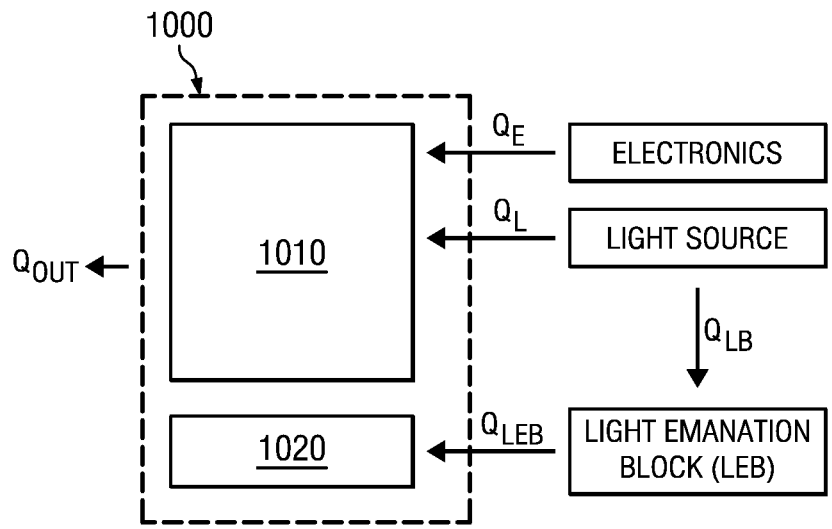
FIG. 10a illustrates in schematic form a heat exchanger and its associated radiant energy and heat transfer paths, in accordance with certain embodiments of the disclosure.
Figure 10B:
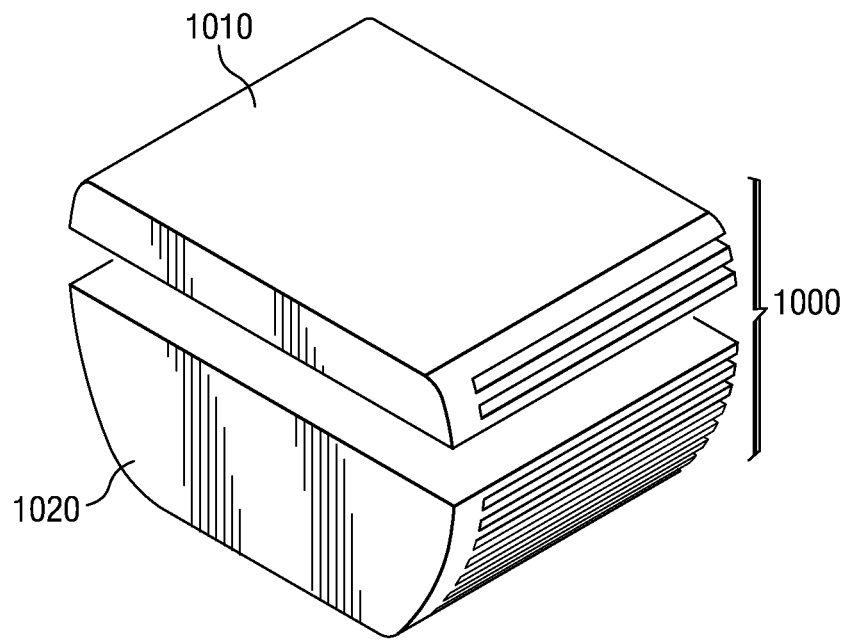
FIG. 10b illustrates in perspective view an exemplary heat exchanger as shown in FIG. 10a, in accordance with certain embodiments of the disclosure.

In accordance with a range of embodiments, there is provided a plurality of heat exchanger blocks for dissipating heat from one or more heat loads within device 10, wherein the number of heat exchanger blocks is greater than one or two. FIGS. 10*a* and 10*b* show an exemplary embodiment of a heat exchanger 1000 having a first heat exchanger block 1010 and a second heat exchanger block 1020. As shown, heat exchanger blocks 1010 and 1020 are separately formed and not substantially thermally coupled. As shown in FIG. 10*a*, block 1010 dissipates heat from both the device electronics and the device light source, and the block 1020 dissipates heat only from the device light emanation block. Blocks 1010 and 1020 may be maintained at the same or different temperatures during all or a portion of device operation.

Figure 9A:
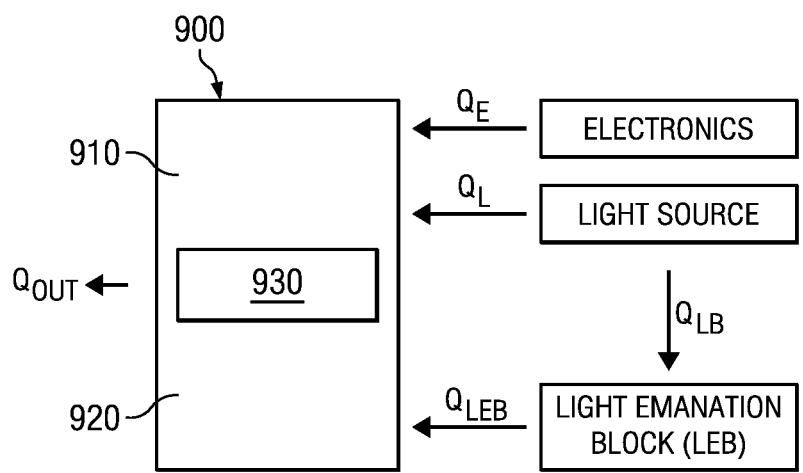
FIG. 9a illustrates in schematic form a heat exchanger and its associated radiant energy and heat transfer paths, in accordance with certain embodiments of the disclosure.
Figure 9B:
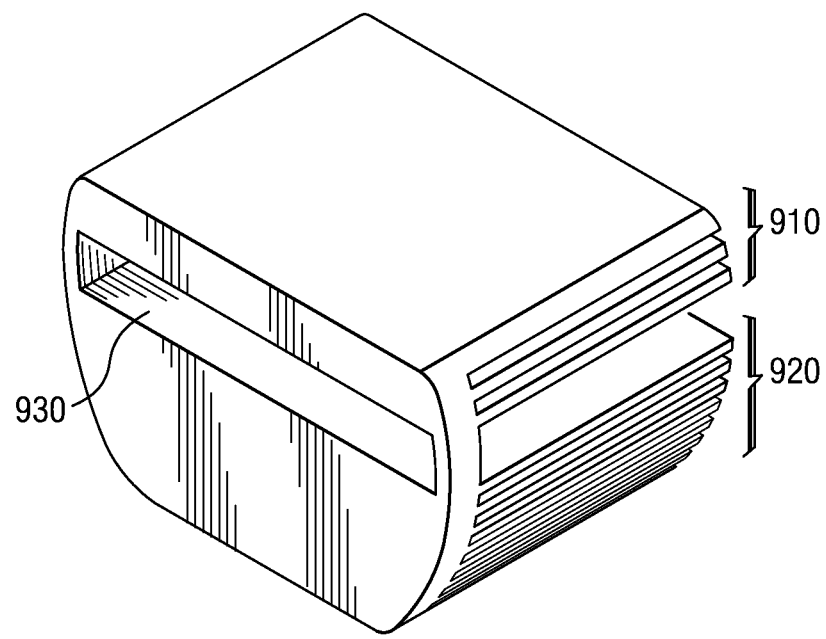
FIG. 9b illustrates in perspective view an exemplary heat exchanger as shown in FIG. 9a, in accordance with certain embodiments of the disclosure.

In accordance with a range of embodiments, the heat exchanger 60 also may include a monolithic block including one or more divides or slots to form a plurality of block regions, so that different temperatures may be maintained across the different regions of the monolithic block. See FIGS. 9*a* and 9*b*. In an embodiment, separate heat loads are associated with each block region, so that each block region is maintained at a temperature optimized to increase device efficiency, enhance device performance, maximize or otherwise obtain a desired rate of heat transfer from its associated heat load, etc. As shown in FIG. 9*a*, heat exchanger block 900 includes a first region 910 and a second region 920 that are coupled in a thermally isolating manner. Isolator 930 as shown, for example, comprises a slot which inhibits heat transfer between regions 910 and 920 and permits different temperatures or the same temperature to be maintained in each region. As shown in FIG. 9*a*, region 910 serves as a heat dissipation conduit for thermal loads $Q_E$ and $Q_L$, and region 920 dissipates heat from the light emanation block or LEB (i.e., thermal load $Q_{LEB}$). One or more fans or other cooling devices may be used in conjunction with the various regions of the heat exchanger block. Thus, in accordance with a range of embodiments of the invention, there is provided a unitary or monolithic heat exchanger block that is partitioned into regions, each region being associated with one or more heat loads from which heat is dissipated, wherein the number of regions is two or greater, and the number of partitions, divides, or slots is one or more.

For device 10 in certain applications, it may be desirable to increase the device coverage rate (i.e., the cross-sectional area of the output window of the device multiplied by the device pulse repetition frequency (PRF)) to enable potentially faster treatment times for a subject area 50 or therapy rates for a device 10. However, increasing device coverage rate by increasing output window area, increasing PRF, or increasing both, would require the device 10 to dissipate the additional amounts of heat associated with such increases. Accordingly, the ability of device 10 to dissipate heat may limit device coverage rate increases, meaning that under such circumstances effective device coverage rate control requires at least in part effective control of heat dissipation.

For a device 10, heat dissipation typically may be a function of the total fin area of heat exchanger 60, the air flow from cooling fan 340, and the temperature difference $\Delta T$ between the heat exchanger fins and the ambient air temperature. Heat dissipation from device 10 occurs both during a light pulse and during the periods before, after, and between light pulses. Accordingly, to increase heat dissipation, one may for example increase the heat exchanger fin size, increase the flow of air from cooling fan 340, or both. Such approaches, however, may be problematic in some instances. Increasing fin size, number, or total area generally results in a larger device, which may not be preferred for a device primarily intended for use as a handheld device. Moreover, altering air flow perhaps requires the device to include a more expensive fan having higher performance characteristics, e.g., air flow volume, size, power consumption, noise, etc. Thus, in accordance with a range of embodiments of the invention, increased or enhanced heat dissipation is achieved by thermal control means, including without limitation increasing the temperature of at least a portion of the heat exchanger, so that the temperature difference $\Delta T$ between exchanger and ambient is increased, or is maintained at increased levels, during operation.

In accordance with a range of embodiments of the invention, one or more parameters, including without limitation one or more of the following temperatures and temperature-related and/or heat transfer-related variables, may be controlled, either alone or in combination, to improve the efficiency and/or performance of device 10: laser diode bar junction temperature, laser diode bar operating temperature, average heat exchanger temperature, light pulse temperature rise, heat exchanger fin temperature, heat exchanger temperature proximate a heat load/heat sink junction, heat exchanger heat capacity proximate the laser diode bar, heat exchanger fin area, airflow proximate the heat exchanger, fan speed, pulse current through the laser diode bar, and the number of laser diode bars.

For the device 10, the amount of energy to be delivered to the skin during a light pulse may be manually entered, may be preset, or may be predetermined (e.g., without limitation, calculated in accordance with specified parameters, set to correspond to one of multiple energy levels wherein such levels may be designated "low," "medium," "high", etc.). Pulse time (i.e., the period of time that the laser diode bar is "on" and light is delivered) may be calculated by dividing the energy setting by the power of the light source. The laser diode bar may be turned on, and the light pulse provided, for such determined period of time. An audible tone, light, or other perceptible alarm or indicator may be used to identify when the laser diode bar turns off and a light pulse ends.

There is a limit to the extent to which the delay between successive light pulses may be reduced. Generally, heat dissipation by the diode bars must occur for the diode bars to operate effectively. The minimum delay period between successive light pulses is the minimally sufficient period that permits such required heat dissipation.

A delay may be introduced between the time skin contact is identified and the time a laser diode bar is turned on to deliver a light pulse. The delay prior to generation of the light pulse may be approximately substantially equal to the time period between successive pulses provided prior to or following the generated light pulse. The delay may exceed the longest of the minimum required periods that occur throughout device operation for heat dissipation.

Associated with the notion of thermal limit delays is a related parameter of sustainable pulse repetition frequency. Sustainable pulse repetition frequency is the minimum rate of light pulse generation required so that operation of the device may continue without the device reaching a thermal limit threshold that would result in introduction of a delay beyond about the delay required for heat dissipation. Generally, in accordance with one range of embodiments of the invention, sustainable pulse repetition frequency may be about one light pulse every 2.5 seconds (i.e., approximately 0.4 pulses/second).

Operation of the device may be controlled to at least initially permit a pulse repetition frequency that is greater than the sustainable pulse repetition frequency. Further, during operation the actual pulse repetition frequency may be monitored and may be either maintained or adjusted upward or downward as circumstances dictate. Preferably, the initial pulse repetition frequency is adjusted downward one or more times over a period of device use, so that sustainable pulse repetition frequency on average is not exceeded. Further, the device 10 may be controlled according to a predetermined absolute pulse repetition limit (for example, one pulse every two seconds). Such absolute limit may be substantially equal to or greater than the longest of the minimum required periods during device operation for heat dissipation.

Certain phototherapy devices may include a temperature sensor associated with the finned heat sink, and may include a restricted mode of operation wherein the heat exchanger is not permitted to exceed a first set point temperature (e.g., 55° C.) for such sensor. That is, the operation of such devices is suspended if the sensed heat exchanger temperature rises above the set point. Further, certain phototherapy devices may include a temperature sensor positioned proximate the tip of the device. Operation of the device may be controlled similarly based upon a second set point temperature associated with the sensed tip temperature (e.g., 37° C.). In addition, certain phototherapy devices may include a temperature sensor positioned proximate a driver circuit board of the device, e.g., to sense power supply temperature. Operation of the device may be controlled similarly based upon a third set point temperature associated with the sensed power supply temperature.

In accordance with a range of embodiments, the device 10 may be controlled in accordance with one or more temperature set points, thermal limits, pulse repetition frequency limits, etc. For illustration, and without limitation, consider the following examples:

Example 1

Initial pulse repetition frequency is one light pulse every two seconds. The device detects that a thermal limit threshold has been reached (e.g., sensed device tip temperature reaches a set point of approximately 37° C.). The pulse repetition frequency is then reduced to one light pulse every 2.5 seconds until either the condition is alleviated (e.g., tip temperature drops below the 37° C. set point) or a second thermal trigger is reached (e.g., tip temperature drops to a specified level). At such time, pulse repetition frequency is increased to greater than one light pulse every 2.5 seconds.

Example 2

Initial pulse repetition frequency is one light pulse every two seconds. The device detects that a thermal limit may be reached (e.g., sensed device tip temperature is increasing toward or is near approximately 37° C.). The pulse repetition frequency is then reduced, or device operation suspended, as necessary to avoid establishment of the thermal limit condition. When a lower thermal trigger of 34° C. is sensed, pulse repetition frequency is increased again to one light pulse every two seconds.

Laser diode bars typically may be about 50% efficient at normal baseline operating temperatures. Thus, by way of example, for a laser diode bar at 25° C., a forty watt (40 W) electrical input results in about a twenty watt (20 W) optical output and a twenty watt (20 W) thermal output. At higher temperatures, though, laser diode bars are less efficient. For example, for a laser diode bar at 42° C., a forty watt (40 W) electrical input produces a sixteen watt (16 W) optical output and a twenty-four watt (24 W) thermal output. To the extent that more heat is produced per light pulse, the time required between successive pulses for heat dissipation to occur will increase. Accordingly, in accordance with a range of embodiments of the present invention, an increase or enhancement of device efficiency or performance may be identified by an increased time period associated with meeting a thermal limit threshold.

In accordance with a certain range of embodiments, the energy provided to the tip of a device 10 for delivery to a subject area may be fixed. Accordingly, improvements or changes in device 10 efficiency or performance may be associated with relative increases or decreases in light pulse time periods. Further, light pulse time period may be varied based upon one or more of laser diode bar operating temperature and heat exchanger temperature.

In accordance with a range of embodiments, light pulse time may be adjusted based upon a sensed temperature within or otherwise associated with operation of the device 10. Pulse repetition frequency may be controlled by allowing a sensed temperature to rise. Further, such rise may occur without regard to a thermal or temperature limit directly associated with the sensed temperature. Under such circumstances of rising temperature, the operation of one or more device components may be adjusted accordingly to achieve a desired operational result. By way of example, and without limitation, as heat exchanger temperature increases, light pulse duration may be maintained or increased. By way of further example without limitation, multiple temperature or other parameters may adjust together, at the same time, or as a result of another such adjustment.

Preferably, in accordance with a range of embodiments of the invention, the difference between heat exchanger and ambient temperatures is adjusted or controlled to establish or to maintain a desired difference. Such adjustment may occur, for example, by providing a shaped heat exchanger including an area of relatively high heat capacity proximate a thermal load, by providing a heat exchanger with a decreased fin area, or both. In certain embodiments, the temperature of the heat exchanger is variable and increases or floats to a relative maximum temperature of greater than 42° C. for at least a portion of the operational period of device 10. In some applications, the maximum float temperature may exceed 46° C., and in others such temperature may exceed one or more of the following temperatures: 55° C. and 60° C. Such temperatures may correspond to light source average operating temperatures (e.g., laser diode bar package average operating temperature) or other temperatures associated with the operation of device 10.

In accordance with a certain range of embodiments, a maximum device tip temperature may serve as a limit on device operation. In one embodiment, sensed tip temperature is established or maintained at a temperature substantially equal to such limit. In accordance with certain embodiments of the invention, sensed tip temperature is controlled in part by allowing heat exchanger temperature to increase without regard to a limit based upon sensed heat exchanger temperature. Alternately, or in addition, sensed tip temperature may be controlled based upon a thermal or other limit associated with the operation of a TE module, fan, or other assembly used to dissipate heat from a heat load within the device 10.

In accordance with certain embodiments, device tip temperature also may be established or maintained at a desired temperature level. Preferably, such level is between about 32° C. and about 37° C. The tip temperature range may vary based upon skin type. Preferably, for skin type II at the maximum sustainable pulse repetition frequency (PRF) the device tip temperature does not exceed 37° C.

For the heat load associated with the device electronics, in certain embodiments the operating temperature at the heat load may increase up to about 150° C. without substantial degradation in performance. On the other hand, the temperature sensitivity of the diode bars and the TE module is much greater. The efficiency of the TE module decreases significantly as the temperature of the heat exchanger proximate the TE module increases. The laser diode bars also become less efficient as operating temperature increases.

For a phototherapy device in accordance with the invention, as described for example in FIG. 1, a change in operating temperature of magnitude ΔT, and changes in heat transfer amounts for one or more of the thermal loads of the device, may relate to overall device heat dissipation as follows:

$$\frac{\Delta Q_L}{\Delta T} + \frac{\Delta Q_{LEB}}{\Delta T} + \frac{\Delta Q_E}{\Delta T} = \frac{\Delta Q_{OUT}}{\Delta T}$$

In such case, maximum heat dissipation would be achieved for the device 10. Accordingly, in accordance with a certain range of embodiments, the device 10 may analyze one or more of the heat transfers occurring within the device as a function of a heat exchanger temperature or the rate of change of such temperature, or a derivative function thereof, appropriately sum the derivatives of such functions, and determine whether a peak heat dissipation condition exists. Moreover, in certain embodiments where a determination is made that a desired condition such as peak heat dissipation fails to exist, the status or operation of the device, or of one or more of its components, may be manually or automatically adjusted to promote the establishment of such condition for the device.

In accordance with certain embodiments of the invention, a variety of thermal elements may be used. In some embodiments, for example, the light emanation block 30 and the heat exchanger 60 are adapted so that use of a TE module is unnecessary. In such case, a portion of the light emanation block 30 may be directly or indirectly coupled to the heat exchanger. For example, a copper block may be operatively coupled between the light emanation block 30 and the heat exchange to promote heat transfer $Q_{LEB}$. Alternately, and by way of further example, the light emanation block 30 and the heat exchanger 60 may be operatively coupled for direct thermal transfer. In such case, the light emanation block 30 may be equipped with, or the barrel 220 may include, relatively high heat conductivity materials adapted to promote heat flow from light emanation block 30 to heat exchanger 60. The heat exchanger 60 also may be similarly equipped to promote effective heat dissipation. Alternately, the heat exchanger 60 may comprise multiple heat exchange structures, with one or more structures dedicated to the removal of heat from light emanation block 30, i.e., heat transfer $Q_{LEB}$. In another range of embodiments, the air flow from fan 340 may be increased, alone or in conjunction with the other measures described herein, to improve the dissipation of heat in transfer $Q_{OUT}$, preferably so that the device tip temperature may be maintained as desired. Again, the particular thermal elements referenced above, the manner of their impact on heat dissipation during device operation, etc., are merely examples in accordance with ranges of embodiments of the invention, and are not limiting.

For the purposes of this disclosure, the device 10 may include an information handling system. The system may include any instrumentality or aggregate of instrumentalities operable to compute, classify, process, transmit, receive, retrieve, originate, switch, store, display, manifest, detect, record, reproduce, handle, or utilize any form of information, intelligence, or data for control or other purposes. For example, an information handling system may include a microcontroller, microprocessor, computer, or other electronic component assembly that includes, e.g., circuitry, memory, software and other programming, either alone or in combination, for device operation and to carry out the methods and steps disclosed. A suitable device or system may vary in size, shape, performance, functionality, and price. The information handling system may include memory, one or more processing resources such as a central processing unit (CPU) or hardware or software control logic. Additional components of the information handling system may include one or more storage devices, one or more communications ports for communicating with external devices as well as various input and output (I/O) devices, such as a keyboard, a mouse, and a display. The information handling system may also include one or more buses operable to transmit communication between the various hardware components of the device 10.

For the purposes of this disclosure, storage or memory devices may include computer-readable media, i.e., any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such wires, optical fibers, microwaves, radio waves, and other electromagnetic and/or optical carriers; and/or any combination of the foregoing.

As mentioned above, information handling systems may utilize LCDs to display data and/or other media. LCDs are often a thin, flat display device made up of any number of color or monochrome pixels arrayed in front of a light source or reflector. Many LCDs also use very small amounts of electric power relative to other types of displays with similar viewable areas. Accordingly, because of their size and power consumption properties, LCDs may be used in battery-powered devices.

An information handling system may generally be operable to receive data from and/or communicate data to one or more other information handling systems via a network or communication path. In certain embodiments, such a system may include a device comprising a processor, a memory communicatively coupled to the processor, a network interface communicatively coupled to processor, and a user interface communicatively coupled to the processor.

A processor may comprise any system, device, or apparatus operable to interpret and/or execute program instructions and/or process data, and may include, without limitation, a microprocessor, microcontroller, digital signal processor (DSP), application specific integrated circuit (ASIC), or any other digital or analog circuitry configured to interpret and/or execute program instructions and/or process data. In some embodiments, the processor may interpret and/or execute program instructions and/or process data stored in a memory and/or another component of the device. A memory may be communicatively coupled to a processor.

A network interface may be any suitable system, apparatus, or device operable to serve as an interface between host device and a network. A network interface may enable a device to communicate over a network using any suitable transmission protocol and/or standard.

A user interface may comprise any instrumentality or aggregation of instrumentalities by which person may interact with the device. For example, a user interface may permit a person to input data and/or instructions into the device (e.g., via a keyboard, pointing device, touchpad, sound or voice interface, and/or other suitable means), and/or otherwise manipulate the device and its associated components. A user interface may also permit the device to communicate data to a person, e.g., by means of a display device.

As will be understood by those skilled in the art who have the benefit of the instant disclosure, other equivalent or alternative devices, methods, and systems for heat transfer can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of light sources, light emanation blocks, heat exchangers, heat transfer regions, thermal converters, and thermoelectric modules, may be varied. In some embodiments, one or more parts may be interchangeable. Interchangeability may allow the heat transfer to be custom adjusted (e.g., by adjusting the number and/or location of heat transfer regions). In addition, the size of a phototherapy device and/or system may be scaled up (e.g., to be used for adult subjects) or down (e.g., to be used for juvenile subjects) to suit the needs and/or desires of a practitioner. Where the verb "may" appears, it is intended to convey an optional and/or permissive condition, but its use is not intended to suggest any lack of operability unless otherwise indicated. Also, where ranges have been provided, the disclosed endpoints may be treated as exact and/or approximations as desired or as demanded by the particular embodiment. Where the endpoints are approximate, the degree of flexibility may vary in proportion to the order of magnitude of the range. For example, a range of endpoint of "about 50" may one the one hand include 50.5, but not 52.5 or 55 in the context of a range of about 5 to about 50 and, on the other hand, include 55, but not 60 or 75 in the context of a range of about 0.5 to about 50. In addition, it may be desirable, in some embodiments, to mix and match range endpoints. Also, in some embodiments, each figure disclosed (e.g., in one or more of the Examples and/or Drawings) may form the basis of a range (e.g., +/−about 10%, +/−about 100%) and/or a range endpoint. According to some embodiments, expressions of a concentration of a material of "up to" (e.g., up to about 10%) includes, at the lower end of the range, any amount of the material greater than zero. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

All or a portion of a device and/or system for heat transfer may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. A phototherapy device comprising:
a light source;
a light emanation block;
an outlet end configured to be placed in contact with a person's skin; and
a heat exchanger including:
a first heat transfer region operatively coupled to the light source for the dissipation of heat from the light source via the first heat transfer region; and
a second heat transfer region operatively coupled to the light emanation block for the dissipation of heat from the light emanation block via the second heat transfer region,
wherein both the light source and the light emanation block are arranged on a forward side of the heat exchanger along a direction extending from the light source to the outlet end of the device, such that both the first heat transfer region and the second heat transfer region are provided on the forward side of the heat exchanger, and such that both the light source and the light emanation block are arranged between the heat exchanger and the outlet end of the device; and
wherein the first heat transfer region and the second heat transfer region are substantially thermally isolated from each other.

2. A phototherapy device according to claim 1, further comprising:
a thermal converter; and
the heat exchanger including a third heat transfer region operatively coupled to the thermal converter for the dissipation of heat from the thermal converter via the third heat transfer region.

3. A phototherapy device according to claim 2, wherein the third heat transfer region is substantially thermally isolated from the first heat transfer region.

4. A phototherapy device according to claim 2, wherein the third heat transfer region is substantially thermally isolated from the second heat transfer region.

5. A phototherapy device according to claim 2, wherein the heat exchanger is a monolithic block, and wherein the third heat transfer region is substantially thermally isolated from the first heat transfer region and from the second heat transfer region.

6. A phototherapy device according to claim 1, further comprising:
a thermoelectric module thermally coupled between the light emanation block and the heat exchanger.

7. A phototherapy device according to claim 1, wherein the first and second heat transfer regions are provided on the same heat exchanger element.

8. A phototherapy device according to claim 1, wherein the heat exchanger includes:
a first heat exchanger element including the first heat transfer region, and
a second heat exchanger element physically distinct from the first heat exchanger element and including the second heat transfer region.

9. A phototherapy device comprising:
a light source that emits light as a result of a controlled stimulated emission;
a light emanation block; and
a heat exchanger including a first heat transfer region thermally coupled to the light source for the dissipation of heat from the light source via the first heat transfer region and a second heat transfer region thermally coupled to the light emanation block for the dissipation of heat from the light emanation block via the second heat transfer region, wherein both the first heat transfer region thermally coupled to the light source and the second heat transfer region thermally coupled to the light emanation block are provided on a first side of the heat exchanger that faces a treatment end of the phototherapy device, such that both the light source and the light emanation block are arranged between the heat exchanger and the treatment end of the device; and wherein the first heat transfer region and the second heat transfer region on the first side of the heat exchanger are substantially thermally isolated from each other.

10. A phototherapy device according to claim 9, wherein the first and second heat transfer regions are provided on the same heat exchanger element.

11. A phototherapy device according to claim 9, wherein the heat exchanger includes:
  a first heat exchanger element including the first heat transfer region, and
  a second heat exchanger element physically distinct from the first heat exchanger element and including the second heat transfer region.

12. A phototherapy device comprising:
  an outlet end configured to be placed in contact with a person's skin;
  a heat exchanger:
  a light emanation structure arranged between the heat exchanger and the outlet end of the device;
  a light source arranged between the heat exchanger and the outlet end of the device, and configured to emit light for delivery to the skin through or adjacent the light emanation structure;
  wherein the heat exchanger comprises:
    a first heat transfer portion thermally coupled to the light source for the dissipation of heat from the light source via the first heat transfer portion; and
    a second heat transfer portion thermally coupled to the thermally conductive structure for the dissipation of heat from the light emanation structure via the second heat transfer portion,
    wherein the first heat transfer portion and the second heat transfer portion are substantially thermally isolated from each other.

13. A phototherapy device according to claim 12, wherein the light emanation structure defines an elongated opening through which the light from the light source is delivered toward the skin.

14. A phototherapy device according to claim 13, wherein the light emanation structure comprises a barrel structure.

15. A phototherapy device according to claim 13, wherein the light emanation structure comprises a mixer through which the light from the light source is delivered toward the skin.

16. A phototherapy device according to claim 12, wherein the first and second heat transfer portions are defined on the same side of the heat exchanger.

17. A phototherapy device according to claim 12, wherein the first and second heat transfer portions are provided on the same heat exchanger element.

18. A phototherapy device according to claim 12, wherein the first and second heat transfer portions comprise physically distinct first and second heat exchanger elements.

19. A phototherapy device according to claim 18, wherein the physically distinct first and second heat exchanger elements extend generally parallel to each other.

* * * * *